US010894137B2

(12) United States Patent
Ramdohr et al.

(10) Patent No.: US 10,894,137 B2
(45) Date of Patent: Jan. 19, 2021

(54) TRACHEAL TUBE AND METHOD OF PRODUCTION

(71) Applicant: Primed Halberstadt Medizintechnik GmbH, Halberstadt (DE)

(72) Inventors: Bastian Ramdohr, Halberstadt (DE); Sascha Leibitzki, Blankenburg (DE)

(73) Assignee: Primed Halberstadt Medizintechnik GmbH, Halberstadt (DE)

( * ) Notice: Subject to any disclaimer, the term of this patent is extended or adjusted under 35 U.S.C. 154(b) by 414 days.

(21) Appl. No.: 15/849,061

(22) Filed: Dec. 20, 2017

(65) Prior Publication Data

US 2019/0184120 A1    Jun. 20, 2019

(51) Int. Cl.
*A61M 16/04*        (2006.01)
*A61M 16/08*        (2006.01)
(Continued)

(52) U.S. Cl.
CPC .... *A61M 16/0402* (2014.02); *A61M 16/0825* (2014.02); *A61M 25/0014* (2013.01);
(Continued)

(58) Field of Classification Search
CPC .............. A61M 16/0402; A61M 39/08; A61M 39/1055; A61M 39/1011; A61M 25/0014; A61M 16/0825; A61M 2039/1027; A61M 25/0041; A61M 16/0427; A61M 16/0465; A61M 16/0463; A61M 16/04; A61M 16/0468; A61M 16/0488; A61M 16/0497; A61M 16/08; A61M 16/0816; A61M 16/0875; A61M 25/0009; A61M 25/0097; A61M 25/02; A61M 2025/024; A61M 39/00; A61M 39/10; A61M 39/12; A61M 2039/1033; A61M 2039/1077
(Continued)

(56) References Cited

U.S. PATENT DOCUMENTS 3,824,999 A * 7/1974 King ................. A61M 16/0465
                                                128/207.17
4,686,977 A * 8/1987 Cosma .............. A61M 16/0465
                                                128/207.17
(Continued)

FOREIGN PATENT DOCUMENTS

DE         19514433 C1    1/1996
DE       102005030300 B3   7/2006

*Primary Examiner* — Justine R Yu
*Assistant Examiner* — Mayisha M Khan
(74) *Attorney, Agent, or Firm* — Cohen & Hildebrand, PLLC

(57) ABSTRACT

It is the object of the invention, which relates to a tracheal tube (1) and a method for producing a tracheal tube (1), to provide a tracheal tube (1) with a connector (3), wherein the connector (3) is connected to a curved tube (2) by way of a rotatable and pivotable connection that can be easily realized. This object is solved with a device having a joint head part (4) of a ball joint arranged on first end of the connector (3) facing the curved tube (2), a first partial socket (2.1) of the ball joint arranged on a first end of the curved tube (2) facing the connector (3), a locking socket (5) arranged as a second partial socket of the ball joint, and a locking ring (6) arranged for connecting the locking socket (5) with the curved tube (2).

11 Claims, 5 Drawing Sheets

(51) Int. Cl.
*A61M 25/00* (2006.01)
*A61M 39/10* (2006.01)
*A61M 39/08* (2006.01)

(52) U.S. Cl.
CPC ........ *A61M 39/08* (2013.01); *A61M 39/1011* (2013.01); *A61M 39/1055* (2013.01); *A61M 25/0041* (2013.01); *A61M 2039/1027* (2013.01)

(58) Field of Classification Search
USPC ..... 128/207.14, 207.15; 604/164.01, 164.02, 604/164.04, 164.07, 164.09–164.11, 604/165.01, 165.02, 165.04
See application file for complete search history.

(56) References Cited

U.S. PATENT DOCUMENTS

| | | | | |
|---|---|---|---|---|
| 5,054,482 A * | 10/1991 | Bales | ............ | A61M 16/0465 128/207.14 |
| 6,053,167 A * | 4/2000 | Waldeck | ............ | A61M 16/0465 128/207.14 |
| 9,010,326 B2 * | 4/2015 | Bruggeman | ...... | A61M 16/0465 128/204.17 |
| 10,322,254 B2 * | 6/2019 | Fong | ............ | A61M 16/0622 |
| 2005/0150497 A1 * | 7/2005 | Eifler | ............ | A61M 16/06 128/206.21 |
| 2008/0041391 A1 * | 2/2008 | Worley | ............ | A61M 16/0465 128/207.14 |
| 2009/0312727 A1 * | 12/2009 | Heaton | ............ | A61M 1/008 604/318 |
| 2010/0108076 A1 * | 5/2010 | Chang | ............ | A61M 16/0465 128/207.17 |
| 2010/0307488 A1 * | 12/2010 | Poulsen | ............ | A61M 16/0465 128/200.26 |
| 2012/0247478 A1 * | 10/2012 | Harrington | ....... | A61M 16/0465 128/207.14 |
| 2016/0038700 A1 * | 2/2016 | White | ............ | A61M 16/0463 128/202.27 |
| 2017/0028155 A1 * | 2/2017 | Bateman | ........ | A61M 16/0465 |
| 2018/0043118 A1 * | 2/2018 | Jeffrey | ........ | A61M 16/0465 |
| 2018/0133425 A1 * | 5/2018 | Bateman | ........ | A61M 16/0465 |

* cited by examiner

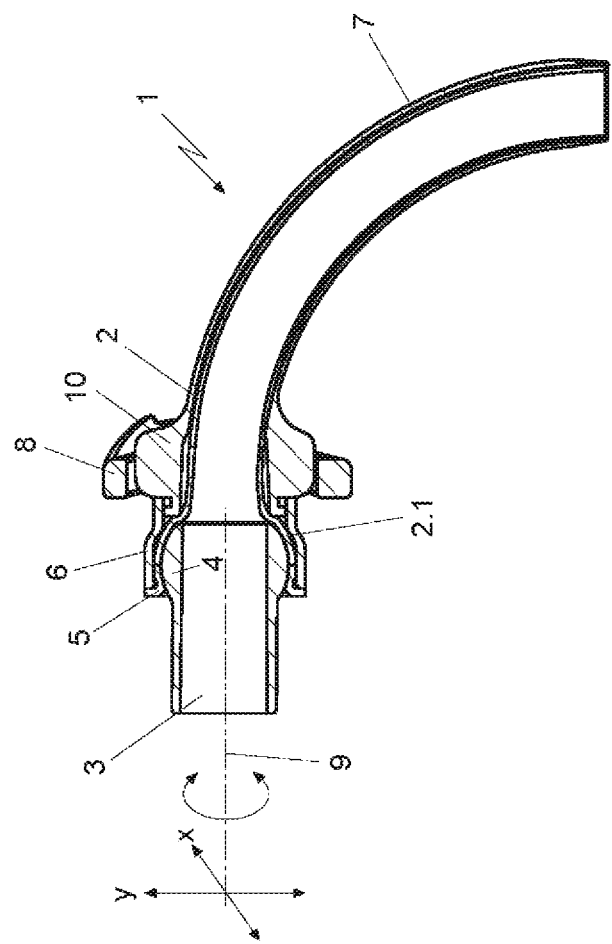
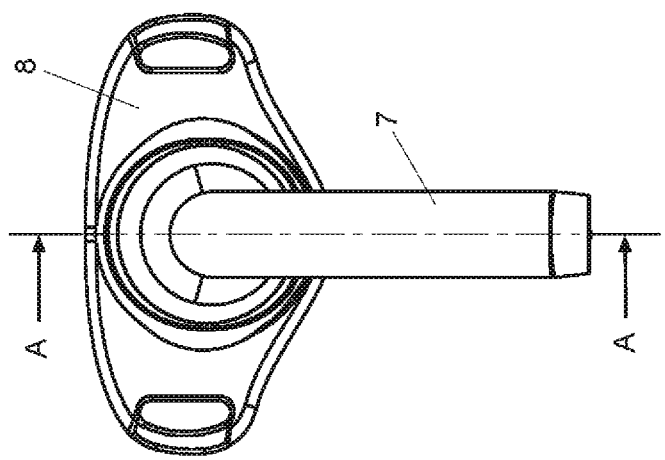
FIG. 2B
FIG. 2A

TRACHEAL TUBE AND METHOD OF PRODUCTION

BACKGROUND OF THE INVENTION

(1) Field of the Invention

The invention relates to a tracheal tube, which has at least one curved tube and a connector.

The invention also relates to a method for producing a tracheal tube, wherein a curved tube is connected to a connector.

(2) Description of Related Art

For example, when long-term ventilation becomes necessary after an accident or surgery, following a neurological disease with a disorder of the swallowing reflex, radiation treatment to the head or neck or in the event of larynx paralysis, a surgical procedure may be required by which an access to the windpipe, also referred to as tracheostoma, is created through the soft tissue of the neck. This medical intervention, colloquially also referred to as windpipe incision, is also performed in the prior art, for example, as a last resort in the event of an obstruction of the upper airways to prevent the patient from suffocating. A tracheostoma is also common in patients after complete removal of the larynx.

It is also known from the prior art to insert and to secure a so-called tracheal tube through a tracheostoma in the trachea, wherein the tracheostoma is kept open by this tracheal tube. Such tracheal tube is usually a flexible to rigid, short, curved hose, which makes breathing possible or easier. If such treatment with a tracheal tube is continued for a longer period, it is also customary to change the tracheal tube on a regular basis.

Tracheal tubes differ, for example, in the type of material used. Usually, materials such as silicone or other plastics or metals such as silver or nickel silver are used for such tubes. The tubes can be further distinguished by their length, inner diameter (lumen), shape and function. The length and the lumen of the tube are customarily adapted to the size of the tracheostoma of the patient. According to the functionality of the tracheal tubes, a distinction can be made between blockable and non-blockable tubes.

In DE 195 14 433 C1, a tracheal tube for use in a tracheostoma is described, which has a tubular aped outer tube, in which a likewise tubular inner tube can be guided and locked with the outer tube at the proximal portion, to thereby form a cannula tube. It is provided that a neck flange adapted to rest against the neck is mounted in the proximal region of the outer tube, through which the proximal part of the outer tube engages.

The object of the document is to improve a generic tracheal tube so that it can be pivoted to a sufficient degree about two spatial axes in a technically feasible manner.

This object is solved by implementing the pivoting motion about the spatial Y-axis by a ring which engages around the outer tube and is rotatably mounted thereon and by implementing the pivoting motion about the X-axis by rotationally supporting the neck flange on the ring. When viewing the neck flange ideally as a ring, the invention is realized in that two rings that can rotated with respect to each other, namely the inner ring with respect to the outer ring (neck flange), are pivotally mounted on the outer tube.

This solution only allows pivoting of a tracheal tube about an X- and a Y-axis by means of a mechanically complex arrangement. Forces caused by twisting a tube attached to the connection part or connector and acting on the tracheal tube are not reduced by the proposed solution and degrade the wear comfort of tracheal tube and possibly also cause pain for the patient.

A tracheal tube with a movable flange is known from DE 10 2005 030 300.

The task to be solved in this document is to provide a tracheal tube with a movable flange which enables improved agility and which has a high mechanical stability even under a continuous load.

As solution for this task, it is proposed that the tracheal tube consists of a tubular or hose-shaped cannula to be guided through a neck and trachea incision in the trachea of a patient, in which a likewise tubular inner tube can be guided and locked with the cannula, and neck flange movably mounted on the cannula, through which the cannula passes, to rest against the neck, with the position of cannula or of the end of the cannula in the trachea of the patient being defined by its abutment on the neck of the patient, wherein the cannula is movably mounted with respect to the neck flange on a side facing the patient.

A disadvantage of this solution is that only movements or differences in position between the part of the tracheal tube arranged inside the patient and the neck flange resting against the patient's neck are compensated. Movements or twists, which are caused by a hose connected to the tracheal tube outside of the patient, cannot be compensated.

BRIEF SUMMARY OF THE INVENTION

The object of the invention is now to provide a tracheal tube with a connector, wherein the connector is arranged with a curved tube by way of a rotatable and pivotal connection that is easy to implement. In addition, this connection should be designed as a non-detachable connection for the intended use of the tracheal tube.

The object is attained by an arrangement having the features according to claim 1 of the independent claims. Further embodiments are recited in the dependent claims 2 to 8.

The object is also attained by a method having the features according to claim 9 of the independent claims. A further embodiment is recited in the dependent claim 10.

It is envisioned to form one end of the connector in the form of a joint head part of a ball joint. In this case, such embodiment may only partially form a joint head of a ball joint, as long as the functionality of the ball joint to be formed is ensured.

To fix this joint head part, a two-piece socket is provided. A first part of this socket or the first partial socket is provided on an end of the curved tube facing the connector. The second part of this socket or the second partial socket is realized by a locking socket.

This makes it possible to arrange the connector with its joint head part formfittingly and movably in both parts of the socket. For fastening the locking socket to the described first end of the curved tube, a closure is provided. According to this embodiment, the connector is on the one hand arranged for pivoting in the spatial X- and Y-directions and on the other hand for rotation about its longitudinal axis. Due to this free agility of the connector, forces originating, for example, from a flexible breathing hose connected to the connector are prevented from acting on the patient. Their negative effects, such as the sensation of pressure or pain in a patient, are thus reduced.

It is intended to provide the closure as a locking ring with means for latching or to implement the closure as a bayonet lock. In one embodiment, this locking ring has on a first end means for latching, such as a bead and a groove, and on a second end a bayonet lock. Such a locking ring thus enables simple assembly and disassembly of tracheal tube.

For example, the first end of the locking ring may engage with its bead in a groove of the locking socket, whereas the locking ring is connected at its second end to the outer tube via a bayonet lock.

Furthermore, it is also envisioned to manufacture the connector, the locking ring and the locking socket of a hard plastic, such as acrylonitrile-butadiene-styrene (ABS). The use of such plastic material allows a robust, highly functional design of the movable connection between the curved tube and the connector. Such hard plastic material is typically understood as having a Shore hardness in the range from 50 Shore-D to 90 Shore-D, preferably in the range between 65 Shore-D and 75 Shore-D. Identical or different materials may be used for the connector, the locking ring and the locking socket locking socket, as long as they satisfy the specified conditions for the Shore hardness.

Furthermore, it is also envisioned to manufacture the curved tube from a soft flexible plastic, such as polyurethane or EVA (ethylene vinyl acetate). Such soft plastic material will be understood as a material having a Shore hardness in the range of 40 Shore-A to 90 Shore-A, preferably 60 Shore-A to 70 Shore-A.

The curved tube also has a curved path that deviates from its longitudinal axis and which is adapted to a customary curved outside tube.

The foregoing features and advantages of this invention will be better understood and appreciated after careful reading of the following detailed description of the preferred non-limiting example embodiments of the invention with the accompanying drawings, which show in:

BRIEF DESCRIPTION OF THE DRAWINGS

FIGS. 2A & 2B: a plan view and a sectional view, respectively, of the embodiment according to FIG. 1, FIG. 3: an partially enlarged sectional view of the connection of the curved tube with the connector according to FIGS. 2A & 2B, FIG. 4: an example of the coupling of the arrangement according to the invention with an outer tube.

DETAILED DESCRIPTION OF THE INVENTION

Figure 1:
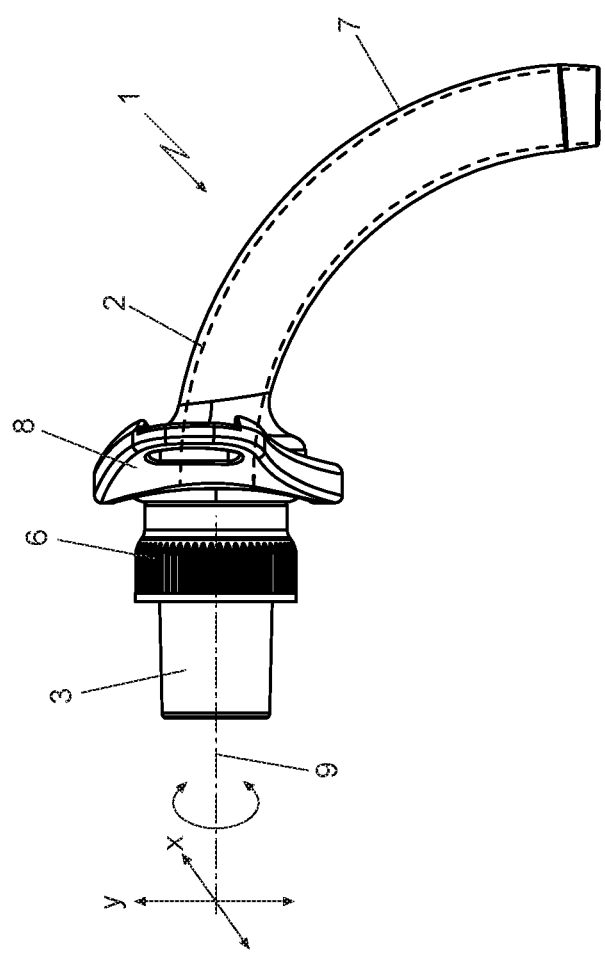
FIG. 1: a schematic diagram of an embodiment of the tracheal tube according to the present invention.

FIG. 1 shows a not-to-scale schematic diagram of an embodiment of the tracheal tube 1 according to the invention. The tracheal tube 1 includes a curved tube 2, indicated by a dashed line. This curved tube 2 may, for example, be arranged inside an outer tube 7, which is arranged through a throat and trachea incision into the trachea of the patient. In this position of the tracheal tube 1, the neck plate 8 rests against the neck of a patient. An arrangement of the curved tube 2 in an outer tube 7 is an option and is not necessarily required for the present invention.

The tracheal tube 1 further includes a closure, which is designed as a locking ring 6, which formfittingly connects the curved tube 2 with the connector 3 such that the connector 3 is connected with the curved tube 2 both for pivoting in the indicated spatial directions X and Y as well as for rotation about its longitudinal axis 9. Such a pivoting movement of the connector 3 that is different from its central alignment is not shown in FIG. 1. The connector 3 is arranged on an end of tracheal tube 1 facing away from a patient. This end is alternatively referred to as the machine-side end.

FIG. 2A is a view of the tracheal tube 1 along the longitudinal axis 9 and FIG. 2B is a sectional view along the illustrated section line A-A.

FIG. 2A thus enables a view onto the curved outer tube 7 and the neck plate 8.

FIG. 2B shows a sectional view of a connector 3, which may be, for example, a customary standard connector 3 with a diameter of 15 millimeters. This connector 3 is designed to have on its first end facing the curved tube 2 a so-called joint head of a ball joint. In this case, this first end of the connector 3 forms only part of a spheroidal joint head of a known ball joint, namely a so-called joint head part 4, as shown in FIG. 2B. The connector 3 also has on this first end an opening oriented toward the curved tube 2.

According to the prior art, a joint head of a ball joint is affixed by arranging the joint head in a so-called socket. This socket which at least partially encloses the joint head is realized in the present invention by two parts or by two partial sockets 2.1 and 5. This allows and facilitates easy assembly or disassembly, i.e. establishing a connection of the curved tube 2 with the connector 3 and releasing this connection.

A first partial socket 2.1 is formed by the first end of the curved tube 2 facing the connector 3. The first end of the connector 3, i.e. the joint head part 4, is inserted or arranged in this first partial socket 2.1. Furthermore, the socket is formed by arranging a locking socket 5, which forms the second partial socket and enables the joint head part 4 of the connector 3 to be formfittingly mounted.

A locking ring 6 is provided for securing the joint head part 4 arranged on the first end of the connector 3 with the first partial socket 2.1 and the locking socket 5. The locking ring 6 may for example be connected to the outer tube 7 in the form of a bayonet closure. This locking ring 6 may, for example, be pushed over the curved tube 2 and over the first partial socket 2.1 and interlock by way of suitable means on the locking socket 5 in the position shown in FIG. 2B. Alternatively, the locking ring 6 may also make the connection to the locking socket 5 in the form of a bayonet closure.

Fixing the locking socket 5 in the indicated position on the first partial socket 2.1 and receiving the joint head part 4, which is partially formed as a ball joint, of the connector 3 in the aforedescribed manner provides a formfitting connection between the curved tube 2 and the connector 3 which can be readily released via the locking ring 6. By virtue of this positive fit, the connector 3 can move both in the spatial directions X and Y as well as rotate about its longitudinal axis 9. Forces exerted on the connector 3 of the tracheal tube 1, for example, by a ventilation hose connected to the connector 3 can be kept away from the patient by virtue of this freedom of movement of the connector 3. This improves the comfort of the tracheal tube 1 and reduces stress on the patient. In addition, the risk of the breathing hose detaching from the connector 3 is reduced by the agility of the connector 3.

It is envisioned to produce the connector 3, the locking ring 6 and the locking socket 5 from a hard, easy-to-process and dimensionally stable plastic, whereas the curved tube 2 is preferably made of a soft plastic. For example, acrylonitrile-butadiene-styrene copolymer (ABS) can be used as a hard plastic.

Figure 3:
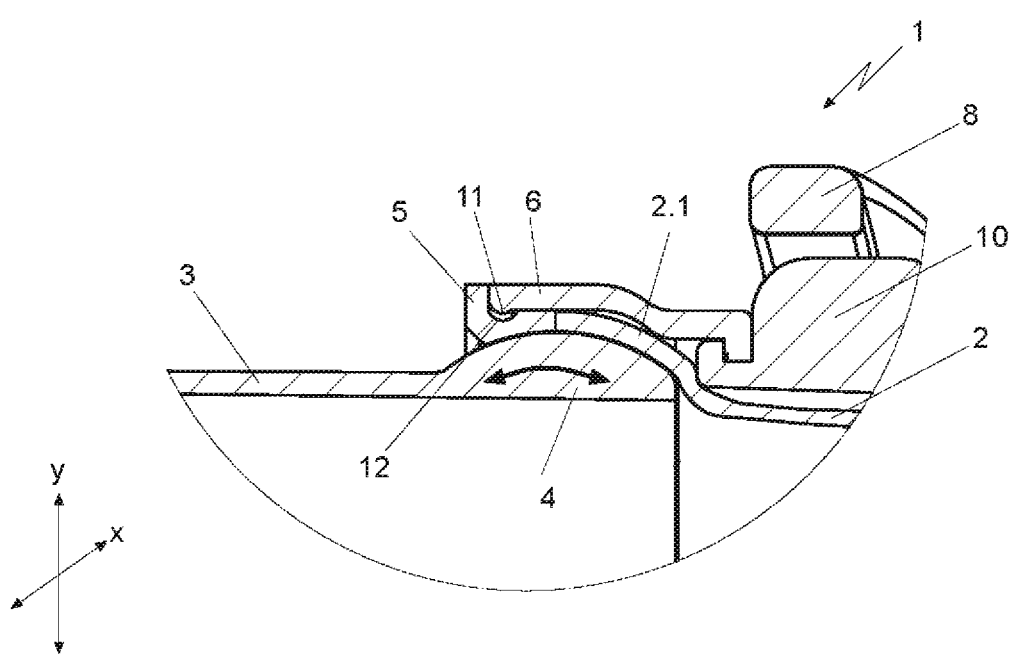

FIG. 3 shows in an enlarged sectional view part of the connection of the curved tube 2 with the connector 3 in accordance with FIG. 2B. Illustrated is the first end of the connector 3 that forms the joint head part 4. As can be seen, this joint head part 4 abuts the first end of the curved tube 2, which forms the first partial socket 2.1. The second partial socket is formed by the locking socket 5. This socket, which is formed by the first and the second partial socket, is dimensioned such that the joint head part 4 of the connector 3 is far enough enclosed so as to produce a formfitting connection which securely holds the joint head part 4 in place. On the other hand, in order to allow the connector 3 to move in the spatial directions X and Y, the joint head part 4 is not completely enclosed by the formed socket.

As an example, the agility of the connector 3 in the spatial direction Y is indicated in FIG. 3 by the double arrow shown in the joint head part 4. The likewise present agility in the spatial direction X as well as the agility about the unillustrated longitudinal axis 9 of the connector 3 have been omitted in FIG. 3, since this is well known to those skilled in technical field of ball joints.

FIG. 3 shows the locking ring 6 which is pushed over the first end of the curved tube 2 and connected to the locking socket 5, and which securely holds the curved tube 2, the locking socket 5 and the connector 3 together after latching in the locking socket 5.

Figure 4:
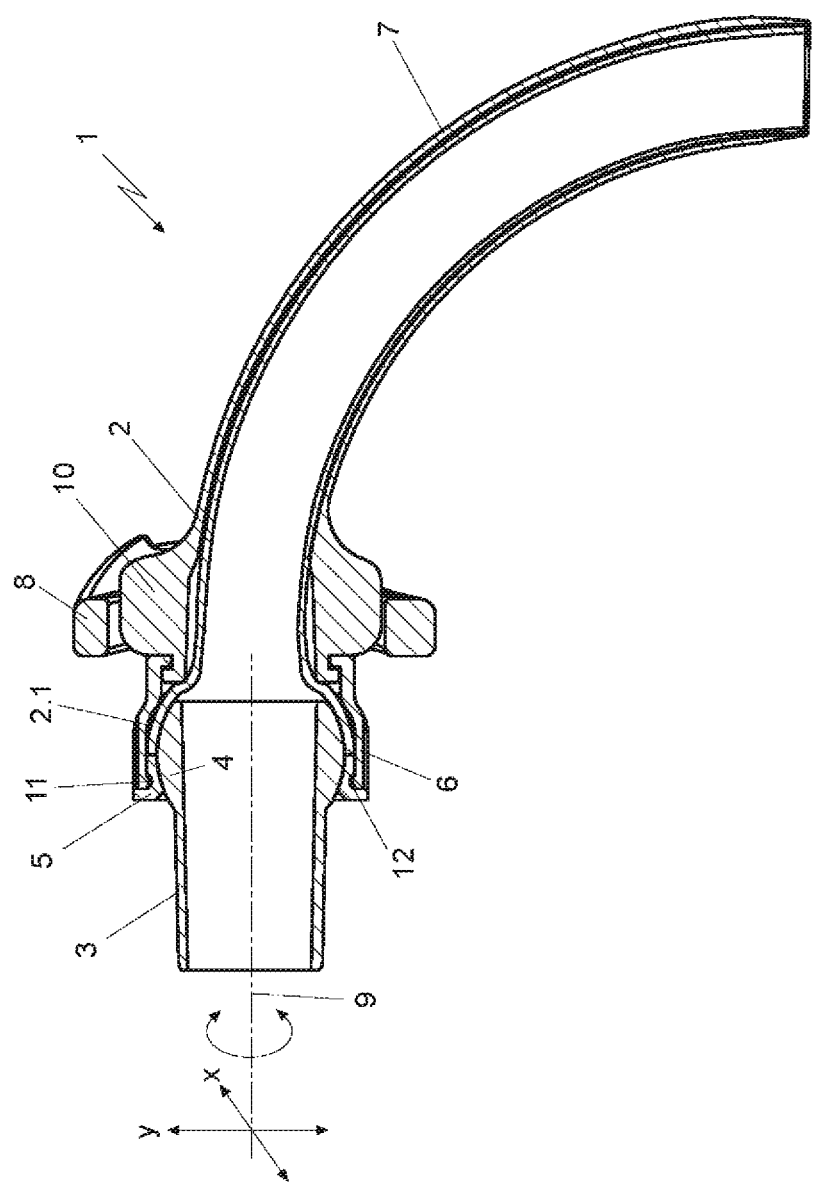

FIG. 4 shows the subsystem composed of the curved tube 2 with the first partial socket 2.1, the locking socket 5, the locking ring 6 and the connector 3 when connected with an outer tube 7.

It is envisioned to connect this subsystem with an outer tube 7 and to thereby complete the system to a functional tracheal tube 1, wherein the outer tube 7 is arranged in a throat and trachea incision of a patient and extends into the trachea of the patient.

For this purpose, the outer tube 7 has, for example, a region with an increasing cross-section 10 where the outer tube 7 is connected with the neck plate 8. A detailed description of this connection has been omitted, since this connection can be implemented in a manner known in the art. In this complete embodiment, the tracheal tube 1 is intended for routine use with a patient, with the neck plate 8 abutting the neck of the patient when the tracheal tube 1 is inserted.

In one embodiment, the locking ring 6 is designed to be connected to the outer tube 7 via a formed bayonet closure. In this way, the locking ring 6 can be pushed, for example, over the part that forms the bayonet closure on the outer tube 7 and secured in a conventional manner by rotation. The end of the locking ring 6 facing away from the bayonet closure may be constructed such that it has an at least partially circumferential bead 11 which reduces the diameter of the locking ring 6. In this case, the locking socket 5 is formed such that it has an at least partially circumferential groove 12 receiving the bead 11. The connection of the locking ring 6 with the locking socket 5 is in this case established by latching the bead 11 of the locking ring 6 in the groove 12 of the locking socket 5. An improved diagram of the elements bead 11 and groove 12 can be seen in FIG. 3.

Alternatively, the connection of the locking ring 6 with the locking socket 5 can also be implemented as a type of bayonet locking ring.

Means, which are necessary or advantageous for the practical implementation of a bayonet locking ring, can be suitably supplemented by a person skilled in the art.

Figure 5:
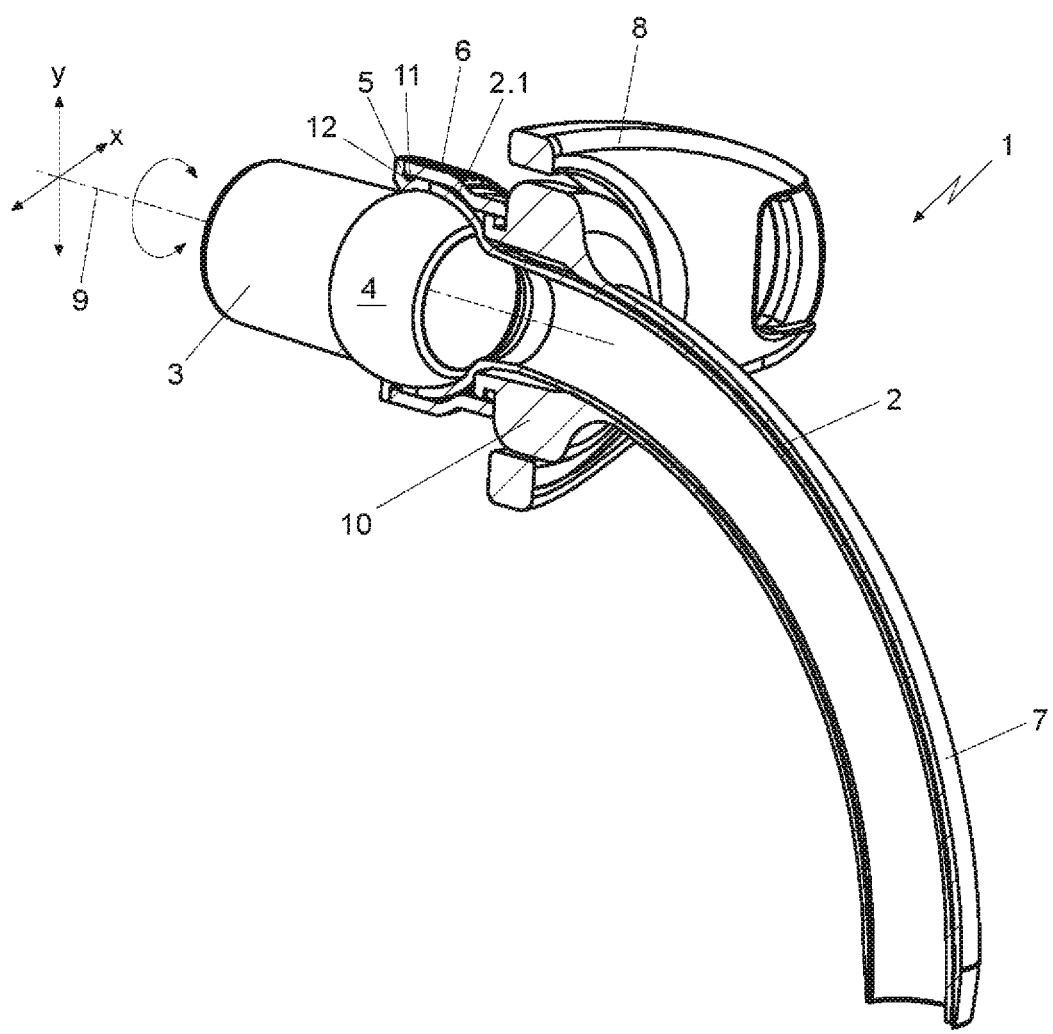
FIG. 5: a perspective view of the tracheal tube according to the invention.

FIG. 5 shows a perspective view of the tracheal tube 1, wherein the connector 3 with its formed joint head part 4 is, unlike all the other elements, not shown in a sectional view. The illustration of FIG. 5 shows in more detail the socket composed of two parts, i.e. of the first partial socket 2.1 and the locking socket 5, in which the joint head part 4 is movably mounted and fixed. This attachment of the joint head part 4 allows the already described pivoting motion of the connector 3 in the spatial directions X and Y and simultaneously its rotation about the longitudinal axis 9. The curved tube 2 arranged in the outer tube 7 can in this embodiment of the arrangement also be designated as inner tube of a tracheal tube 1.

LIST OF REFERENCE SYMBOLS 1 tracheal tube
2 curved tube
2.1 first partial socket
3 connector
4 joint head part
5 locking socket (second partial socket)
6 locking ring
7 outer tube
8 neck plate
9 longitudinal axis
10 region of increasing cross section
11 bead
12 groove

The invention claimed is:

1. A tracheal tube (1), which comprises:
at least one curved tube (2),
a connector (3),
wherein the connector (3) has a first end facing the curved tube (2) forming a joint head part (4) of a ball joint,
wherein the curved tube (2) has a first end facing the connector (3) forming a first partial socket (2.1) of the ball joint,
a locking socket (5) arranged as a second partial socket of the ball joint, and
a locking ring (6) connecting the locking socket (5) with the curved tube (2).

2. The tracheal tube (1) according to claim 1, comprising a first latch securing a first end of the locking ring (6) on the locking socket (5).

3. The tracheal tube (1) according to claim 2, wherein the first latch comprises a bead (11) and a groove (12).

4. The tracheal tube (1) according to claim 1, further comprising an outer tube (7) surrounding the curved tube (2), and a second latch securing a second end of the locking ring (6) on the outer tube (7).

5. The tracheal tube (1) according to claim 4, wherein the second latch is a bayonet closure.

6. The tracheal tube (1) according to claim 1, wherein the curved tube (2) is composed of a soft plastic having a Shore hardness of 40 Shore-A to 90 Shore-A and comprises a bend.

7. The tracheal tube (1) according to claim 1, wherein the connector (3), the locking ring (6) and the locking socket (5) are made of acrylonitrile-butadiene-styrene.

8. The tracheal tube (1) according to claim 1, wherein the connector (3) has at a second end a diameter of about 15 mm.

9. A method for producing a tracheal tube (1), comprising the steps of:
providing a connection between a curved tube (2) and a connector (3), wherein the connector (3) is provided on a first end facing the curved tube (2) with a joint head part (4) of a ball joint, wherein the curved tube (2) is provided on a first end facing the connector (3) a first partial socket (2.1), wherein a locking socket (5) is provided as a second partial socket of the ball joint, wherein the joint head part (4) of the connector (3) is formfittingly and movably secured by the two partial sockets (2.1; 5), wherein the second partial socket is connected to the curved tube (2) by a locking ring (6), and mounting the connector (3) with the joint head part (4) so as to be pivotable in spatial directions X and Y and rotatable about its longitudinal axis (9).

10. The method according to claim 9, wherein the locking ring (6) is provided on a first end with a latch for securing on the second partial socket (5) and wherein the locking ring (6) is provided on a second end with a bayonet closure for securing on an outer tube (7) surrounding the curved tube (2).

11. The tracheal tube (1) according to claim 6, wherein the soft plastic has a Shore hardness of 60 Shore-A to 70 Shore-A.

* * * * *